(12) United States Patent
Hong et al.

(10) Patent No.: US 7,423,263 B2
(45) Date of Patent: Sep. 9, 2008

(54) PLANAR VIEW SAMPLE PREPARATION

(75) Inventors: Liang Hong, Hillsboro, OR (US); Craig Henry, Aloha, OR (US); Jay Jordan, Beaverton, OR (US); Young-Chung Wang, Hillsboro, OR (US)

(73) Assignee: FEI Company, Hillsboro, OR (US)

( * ) Notice: Subject to any disclaimer, the term of this patent is extended or adjusted under 35 U.S.C. 154(b) by 314 days.

(21) Appl. No.: 11/474,519

(22) Filed: Jun. 23, 2006

(65) Prior Publication Data

US 2008/0073535 A1    Mar. 27, 2008

(51) Int. Cl.
G01N 1/28 (2006.01)
H01J 37/20 (2006.01)

(52) U.S. Cl. .................. 250/304; 250/307; 250/311; 250/442.11

(58) Field of Classification Search ................ 250/304, 250/307, 311, 442.11
See application file for complete search history.

(56) References Cited

U.S. PATENT DOCUMENTS

| | | | |
|---|---|---|---|
| 5,270,552 A | 12/1993 | Ohnishi et al. | |
| 5,435,850 A | 7/1995 | Rasmussen | |
| 5,851,413 A | 12/1998 | Casella et al. | |
| 6,140,652 A | 10/2000 | Shlepr | |
| 6,420,722 B2 | 7/2002 | Moore et al. | |
| 6,538,254 B1 | 3/2003 | Tomimatsu et al. | |
| 6,570,170 B2 | 5/2003 | Moore | |
| 6,864,552 B2 | 12/2003 | Shichi et al. | |
| 6,781,125 B2 | 8/2004 | Tokuda et al. | |
| 6,870,161 B2 | 3/2005 | Adachi et al. | |
| 6,927,400 B2 * | 8/2005 | Rasmussen | 250/442.11 |
| 7,015,483 B2 * | 3/2006 | Suzuki et al. | 250/311 |
| 7,041,985 B1 * | 5/2006 | Wang et al. | 250/442.11 |
| 7,067,823 B2 * | 6/2006 | Iwasaki et al. | 250/442.1 |
| 2002/0121614 A1 | 9/2002 | Moore | |
| 2002/0166976 A1 | 11/2002 | Sugaya | |
| 2004/0144924 A1 | 7/2004 | Assalbergs et al. | |
| 2006/0000973 A1 | 1/2006 | Tappel | |
| 2006/0017016 A1 | 1/2006 | Tappel | |

* cited by examiner

Primary Examiner—Jack I Berman
(74) Attorney, Agent, or Firm—Scheinberg & Griner, LLP; David Griner; Michael O. Scheinberg

(57) ABSTRACT

A method and apparatus is described for orienting samples for charged particle beam operations. A sample is attached to a probe with a major surface of the sample at a non-normal angle to the probe shaft, and the probe shaft is rotated to reorient the sample. The invention is particularly useful for preparing planar view TEM samples. The invention allows for a sample to be mounted to a TEM grid and thinning by an ion beam without removing the grid from the vacuum chamber for reorienting. In one embodiment, a probe oriented at an angle, such as 45 degrees, to the sample stage has a probe tip with a flat area oriented parallel at 45 degrees to the probe axis, that is, the flat area is parallel to the sample stage. The flat area of the probe tip is attached to the sample, and when the probe is rotated 180 degrees, the orientation of the sample changes by 90 degrees, from horizontal to vertical. The sample can then be attached to a vertically oriented TEM grid on a sample stage. The sample stage is rotated and tilted to present the backside of the sample to the ion beam for thinning.

17 Claims, 9 Drawing Sheets

PLANAR VIEW SAMPLE PREPARATION

TECHNICAL FIELD OF THE INVENTION

The present invention relates to preparation of samples for viewing in charged particle beam systems.

BACKGROUND OF THE INVENTION

Charge particle beam microscopy, such as scanning ion microscopy and electron microscopy, provides significantly higher resolution and greater depth of focus than optical microscopy. In a scanning electron microscope (SEM), a primary electron beam is focused to a fine spot that scans the surface to be observed. Secondary electrons are emitted from the surface as it is impacted by the primary electron beam. The secondary electrons are detected, and an image is formed, with the brightness at each point on the image being determined by the number of secondary electrons detected when the beam impacts a corresponding spot on the surface. Scanning ion microscopy (SIM) is similar to scanning electron microscopy, but an ion beam is used to scan the surface and eject the secondary electrons.

In a transmission electron microscope (TEM), a broad electron beam impacts the sample and electrons that are transmitted through the sample are focused to form an image of the sample. The sample must be sufficiently thin to allow many of the electrons in the primary beam to travel though the sample and exit on the opposite site. Samples are typically less than 100 nm thick.

In a scanning transmission electron microscope (STEM), a primary electron beam is focused to a fine spot, and the spot is scanned across the sample surface. Electrons that are transmitted through the work piece are collected by an electron detector on the far side of the sample, and the intensity of each point on the image corresponds to the number of electrons collected as the primary beam impacts a corresponding point on the surface.

Because a sample must be very thin for viewing with transmission electron microscopy (whether TEM or STEM), preparation of the sample can be delicate, time consuming work. The term "TEM" sample as used herein refers to a sample for either a TEM or an STEM and references to preparing a sample for a TEM are to be understood to also include preparing a sample for viewing on an STEM. One method of preparing a TEM sample is to cut the sample from a substrate using an ion beam. A probe is attached to the sample, either before or after the sample has been entirely freed. The probe can be attached, for example, by static electricity, FIB deposition, or an adhesive. The sample, attached to the probe, is moved away from the substrate from which it was extracted and typically attached to a TEM grid using FIB deposition, static electricity, or an adhesive.

FIG. 1 shows a typical TEM grid 100, which comprises a partly circular 3 mm ring. In some applications, a sample 104 is attached to a finger 106 of the TEM grid by ion beam deposition or an adhesive. The sample extends from the finger 106 so that in a TEM (not shown) an electron beam will have a free path through the sample 104 to a detector under the sample. The TEM grid is typically mounted horizontally onto a sample holder in the TEM with the plane of the TEM grid perpendicular to the electron beam, and the sample is observed.

Some dual beam systems include an ion beam that can be used for extracting the sample, and an electron beam that can be used for SEM or STEM observation. In some dual beam systems, the FIB is oriented an angle, such as 52 degrees, from the vertical and an electron beam column is oriented vertically. In other systems, the electron beam column is tilted and the FIB is oriented vertically or also tilted. The stage on which the sample is mounted can typically be tilted, in some systems up to about 60 degrees.

TEM samples can be broadly classified as "planar view" samples or "cross sectional view" samples, depending on how the sample was oriented on the work piece. If the face of the sample to be observed was parallel to the surface of the work piece, the sample is referred to as a "planar view" sample. If the face to be observed was perpendicular to the work piece surface, the sample is referred to as a "cross sectional view" sample.

FIG. 2 shows a cross-sectional view TEM sample 200 that is partly extracted from a work piece 202 using a typical process. An ion beam 204 cuts trenches 206 and 208 on both side of sample to be extracted, leaving a thin lamella 210 having a major surface 212 that will be observed by an electron beam. The sample 200 is then freed by tilting the work piece 202 in relation to an ion beam, and cutting around its sides and bottom. A probe 216 attaches to the top of the sample 200, before or after it is freed, and transports the sample to a TEM grid. FIG. 2 shows sample 200 almost entirely freed, remaining attached by a tab 218 on one side. FIG. 2 shows ion beam 204 ready to sever tab 218.

As shown in FIG. 2, the major surface 212 is oriented vertically. Transporting the lamella typically does not change its orientation, so its major surfaces are still oriented vertically when the sample 200 is brought to a TEM sample holder. The plane of the TEM grid 100 is typically oriented vertically as shown in FIG. 3, so that the sample 200 can be attached to the TEM grid in such a way that major surface 212 extends parallel to the plane of the grid, and the grid structure will not interfere with the transmission of electrons when the grid is mounted in a TEM. The ion beam can be used to attach the extracted sample to the TEM grid by ion beam deposition. Once attached, the face of the sample 200 can also be thinned using the ion beam. FIG. 3 shows the sample 200 being attached to the TEM grid 100 in a grid support 302 on a sample stage 304. Sample 200 is attached to grid using an ion beam 204 and a deposition precursor gas 310 from a nozzle 312. FIG. 4 shows that the stage 304 is rotated and tilted so that the sample 200 is perpendicular to the ion beam 204 so that the sample 200 can be thinned by the ion beam.

FIG. 5 shows a work piece 500 from which a planar view sample 502 is being extracted to view a face 504 of the sample. The sample 502 is undercut by two intersecting ion beam cuts 506A and 506B from opposite directions, and then the ion beam cuts the sides 508A and 508B to free a "chunk." A probe 510 is attached to the top of the sample 502. The extracted sample is therefore oriented horizontally. If the sample were attached in a horizontal orientation to a vertically oriented TEM grid, the sample would extend normal to the plane of the grid, and the grid would interfere with the electron beam of the TEM. If the sample were mounted in a horizontally oriented TEM grid, the face 504 to be observed would face upward. It would then be difficult in a conventional FIB system to thin the back side of the planar sample 502 without removing the TEM grid from the vacuum chamber and flipping it over to expose the back side of sample 502 for thinning.

This problem of the orientation of a planar view TEM sample 502 has been overcome in the past by using a "flip stage," on which the TEM grid can be oriented horizontally for attaching the planar view sample, and then the stage can be flipped 180 degrees and rotated so that the backside of the sample can be presented normal to the ion beam for thinning.

A flip stage is described for example in U.S. Pat. App. Pub. No. 20040144924 of Asselbergs et al. for "Method for the manufacture and transmissive irradiation of a sample, and particle-optical system" and provides a degree of freedom not available on conventional stages. Such flip stages are not available in all FIB systems.

Thus, it is desirable to provide a method and apparatus for attaching a planar view sample to a TEM grid in a manner such that the sample can be thinned without reorienting the TEM sample holder.

SUMMARY OF THE INVENTION

An object of the invention is to provide a method and apparatus for altering the orientation of a charged particle beam sample.

This invention facilitates altering the orientation a charged particle beam sample in a charged particle beam system and is useful, for example, for preparing a planar view TEM sample. In one embodiment, a probe comprising a shaft and having an angled tip define is attached to the sample. By rotating the shaft through a first angle, the sample orientation is rotated by a second angle. Knowing the orientation of the longitudinal shaft axis with respect to the sample stage plane, and knowing the angle of the probe tip with respect to the longitudinal shaft axis, one can determine an angle of rotation of the shaft that will rotate the sample orientation by precisely ninety degrees or by any other desired angle. For example, if the longitudinal axis of the shaft is oriented at 45 degrees with respect to the sample stage plane, and the probe tip surface is oriented at 45 degrees with respect to the shaft longitudinal axis, then by rotating the probe shaft 180 degrees, the sample is orientation is altered by ninety degrees, from horizontal to vertical. The sample can be rotated so that it is at a convenient angle for attaching to a TEM grid so that the sample can be thinned by a charged particle beam system without removing the sample from the system for reorientation and without requiring a special stage. Reorienting the sample can facilitate subjecting the sample to other processing, such as laser processing or scanning electron beam microscopy, and the invention is not limited to preparing TEM samples.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more through understanding of the present invention, and advantages thereof, reference is now made to the following descriptions taken in conjunction with the accompanying drawings, in which.

DETAILED DESCRIPTION OF PREFERRED EMBODIMENTS

This disclosure relates to novel methods for altering the orientation of a sample in a charged particle beam system. In one embodiment, the invention facilitates preparation of a planar view sample for viewing in TEMs or STEMs. The methods provide for extracting and mounting a planar view sample onto a TEM grid in such a manner that the sample can be extracted, attached, and thinned without requiring a flip stage and without requiring that the TEM grid to be removed from the vacuum chamber and reoriented. Re-orienting the sample may also facilitate other analytical or processing operations on the sample.

Figure 6:
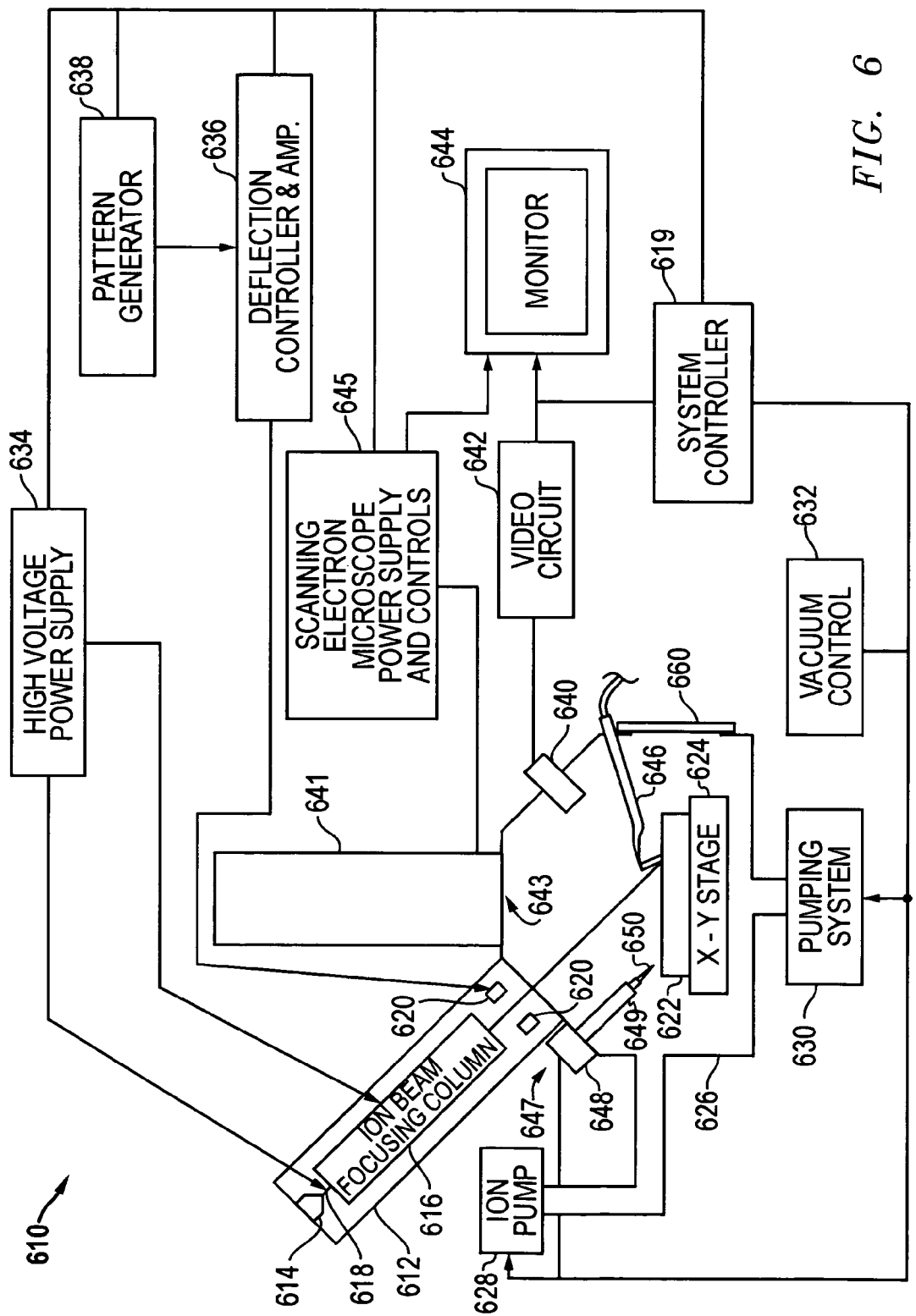
FIG. 6 shows a typical dual beam system used to implement the present invention.

FIG. 6 shows a typical ion beam system, focused ion beam (FIB) system 610, suitable for practicing the present invention. FIB system 610 includes an evacuated envelope having an upper neck portion 612 within which are located a liquid metal ion source 614 or other ion source and a focusing column 616. Other types of ion sources, such as multicusp or other plasma sources, and other optical columns, such as shaped beam columns, could also be used, as well as electron beam and laser system.

An ion beam 618 passes from liquid metal ion source 614 through ion beam focusing column 616 and between electrostatic deflection means schematically indicated at deflection plates 620 toward work piece 622, which comprises, for example, a semiconductor device positioned on stage 624 within lower chamber 626. Stage 624 can also support one or more TEM sample holders, so that a sample can be extracted from the semiconductor device and moved to a TEM sample holder. Stage 624 can preferably move in a horizontal plane (X and Y axes) and vertically (Z axis). Stage 624 can also tilt approximately sixty (60) degrees and rotate about the Z axis. A system controller 619 controls the operations of the various parts of FIB system 610. Through system controller 619, a user can control ion beam 618 to be scanned in a desired manner through commands entered into a conventional user interface (not shown). Alternatively, system controller 619 may control FIB system 610 in accordance with programmed instructions.

For example, a user can delineate a region of interest on a display screen using a pointing device, and then the system could automatically perform the steps described below to extract a sample. In some embodiments, FIB system 610 incorporates image recognition software, such as software commercially available from Cognex Corporation, Natick, Mass., to automatically identify regions of interest, and then the system can manually or automatically extract samples in accordance with the invention. For example, the system could automatically locate similar features on semiconductor wafers including multiple devices, and take samples of those features on different (or the same) devices.

An ion pump 628 is employed for evacuating upper neck portion 612. The lower chamber 626 is evacuated with turbomolecular and mechanical pumping system 630 under the control of vacuum controller 632. The vacuum system provides within lower chamber 626 a vacuum of between approximately $1\times10^{-7}$ Torr ($1.3\times10^{-7}$ mbar) and $5\times10^{-4}$ Torr ($6.7\times10^{-4}$ mbar). If an etch-assisting gas, an etch-retarding gas, or a deposition precursor gas is used, the chamber background pressure may rise, typically to about $1\times10^{-5}$ Torr ($1.3\times10^{-5}$ mbar).

High voltage power supply 634 is connected to liquid metal-ion source 614 as well as to appropriate electrodes in ion beam focusing column 616 for forming an approximately 1 keV to 60 keV ion beam 618 and directing the same toward a sample. Deflection controller and amplifier 636, operated in accordance with a prescribed pattern provided by pattern generator 638, is coupled to deflection plates 620 whereby ion beam 618 may be controlled manually or automatically to trace out a corresponding pattern on the upper surface of work piece 622. In some systems the deflection plates are placed before the final lens, as is well known in the art. Beam blanking electrodes (no shown) within ion beam focusing column 616 cause ion beam 618 to impact onto blanking aperture (not shown) instead of target 622 when a blanking controller (not shown) applies a blanking voltage to the blanking electrode.

The liquid metal ion source 614 typically provides a metal ion beam of gallium. The source typically is capable of being focused into a sub one-tenth micrometer wide beam at work piece 622 for either modifying the work piece 622 by ion milling, enhanced etch, material deposition, or for the purpose of imaging the work piece 622. A charged particle detector 640, such as an Everhart Thornley or multi-channel plate, used for detecting secondary ion or electron emission is connected to a video circuit 642 that supplies drive signals to video monitor 644 and receiving deflection signals from controller 619.

The location of charged particle detector 640 within lower chamber 626 can vary in different embodiments. For example, a charged particle detector 640 can be coaxial with the ion beam and include a hole for allowing the ion beam to pass. In other embodiments, secondary particles can be collected through a final lens and then diverted off axis for collection. A scanning electron microscope (SEM) 641, along with its power supply and controls 645, are optionally provided with the FIB system 610.

A gas delivery system 646 extends into lower chamber 626 for introducing and directing a gaseous vapor toward work piece 622. U.S. Pat. No. 5,851,413 to Casella et al. for "Gas Delivery Systems for Particle Beam Processing," assigned to the assignee of the present invention, describes a suitable gas delivery system 646. Another gas delivery system is described in U.S. Pat. No. 5,435,850 to Rasmussen for a "Gas Injection System," also assigned to the assignee of the present invention. For example, iodine can be delivered to enhance etching, or a metal organic compound can be delivered to deposit a metal.

A micromanipulator 647, such as the AutoProbe 200™ from Omniprobe, Inc., Dallas, Tex., or the Model MM3A from Kleindiek Nanotechnik, Reutlingen, Germany, can precisely move objects within the vacuum chamber. Micromanipulator 647 may comprise precision electric motors 648 positioned outside the vacuum chamber to provide X, Y, Z, and theta control of a portion 649 positioned within the vacuum chamber. The micromanipulator 647 can be fitted with different end effectors for manipulating small objects. In the embodiments described below, the end effector is a thin probe 650. The thin probe 650 may be electrically connected to system controller 619 to apply an electric charge to the probe 650 to control the attraction between a sample and the probe.

A door 660 is opened for inserting work piece 622 onto X-Y stage 624, which may be heated or cooled, and also for servicing an internal gas supply reservoir, if one is used. The door is interlocked so that it cannot be opened if the system is under vacuum. The high voltage power supply provides an appropriate acceleration voltage to electrodes in ion beam focusing column focusing 616 for energizing and focusing ion beam 618. When it strikes work piece 622, material is sputtered, that is physically ejected, from the sample. Alternatively, ion beam 618 can decompose a precursor gas to deposit a material. Focused ion beam systems are commercially available, for example, from FEI Company, Hillsboro, Oreg., the assignee of the present application. While an example of suitable hardware is provided above, the invention is not limited to being implemented in any particular type of hardware.

Figure 1:
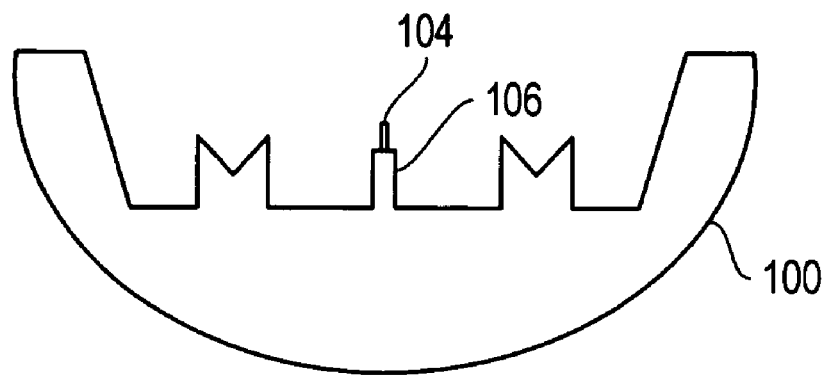
FIG. 1 shows a typical TEM grid to which a sample is attached.
Figure 2:
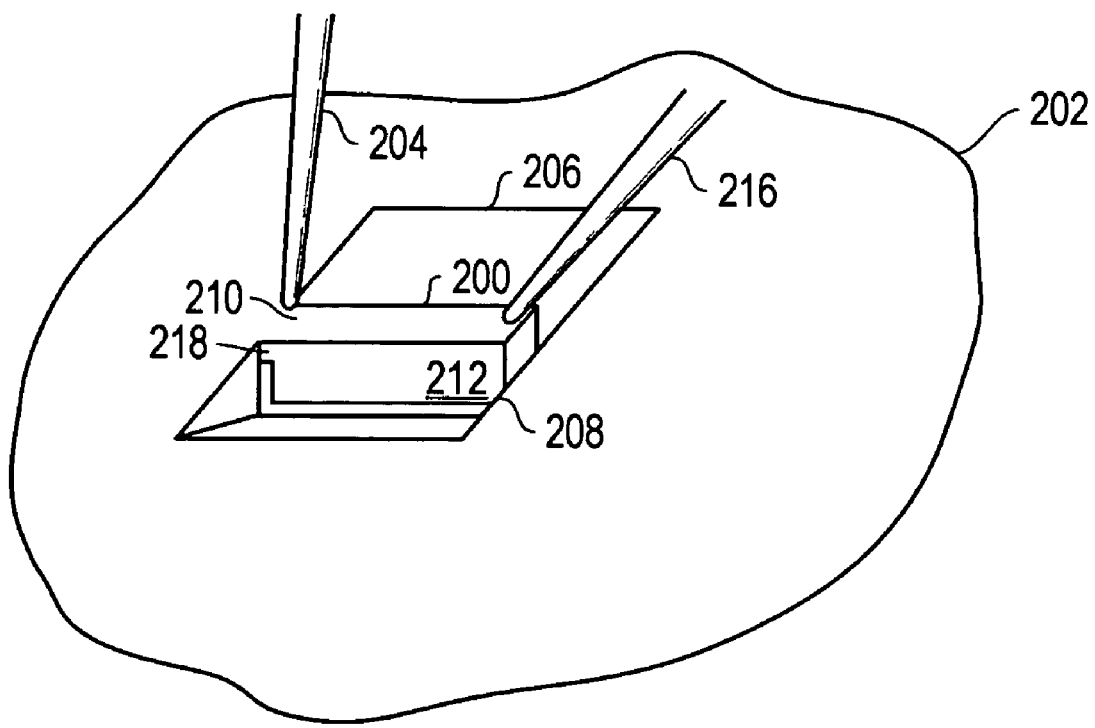
FIG. 2 shows a cross-sectional TEM sample being extracted from a work piece.
Figure 3:
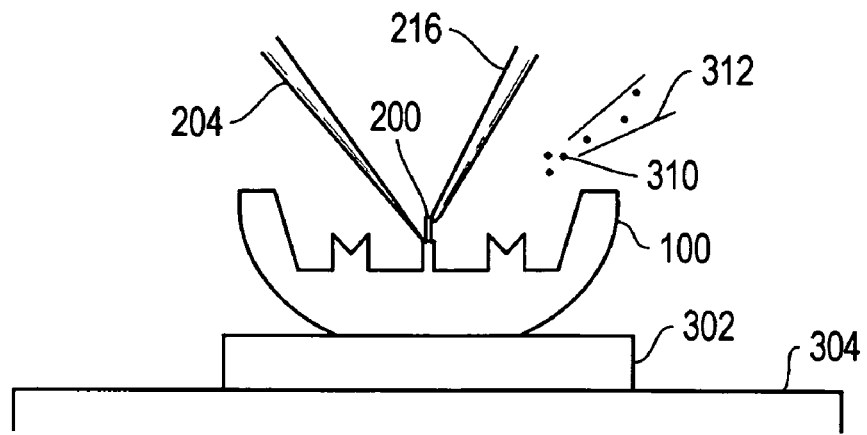
FIG. 3 shows the cross-sectional TEM sample of FIG. 2 being mounted on the TEM grid of FIG. 1.
Figure 4:
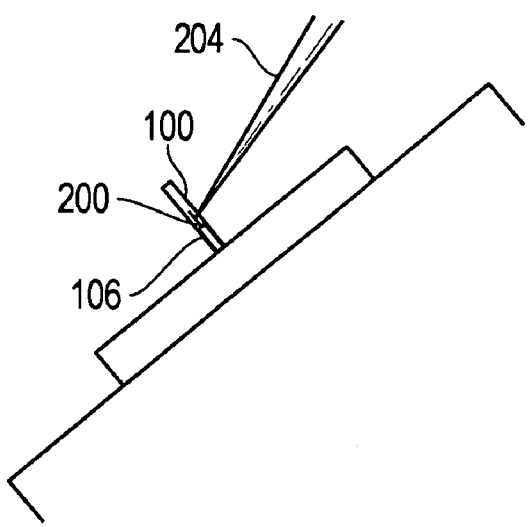
FIG. 4 shows the sample and grid of FIG. 3 tilted and rotated for thinning the sample using an ion beam.
Figure 5:
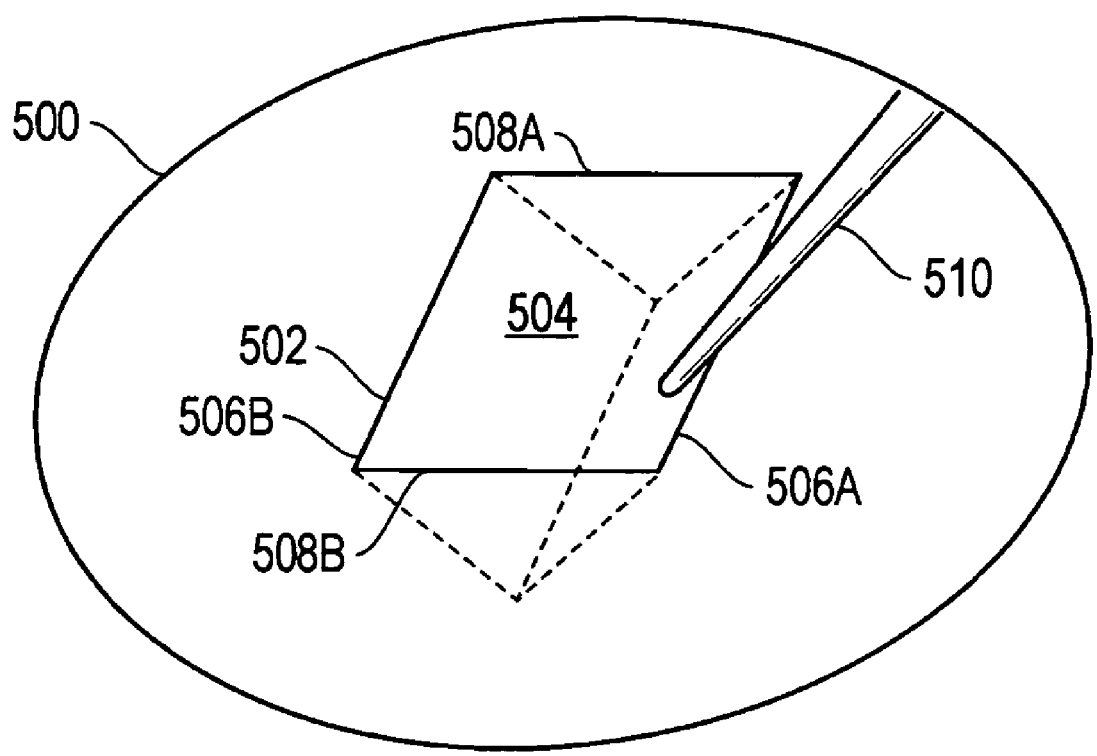
FIG. 5 shows a planar view TEM sample being extracted from a work piece.
Figure 7:
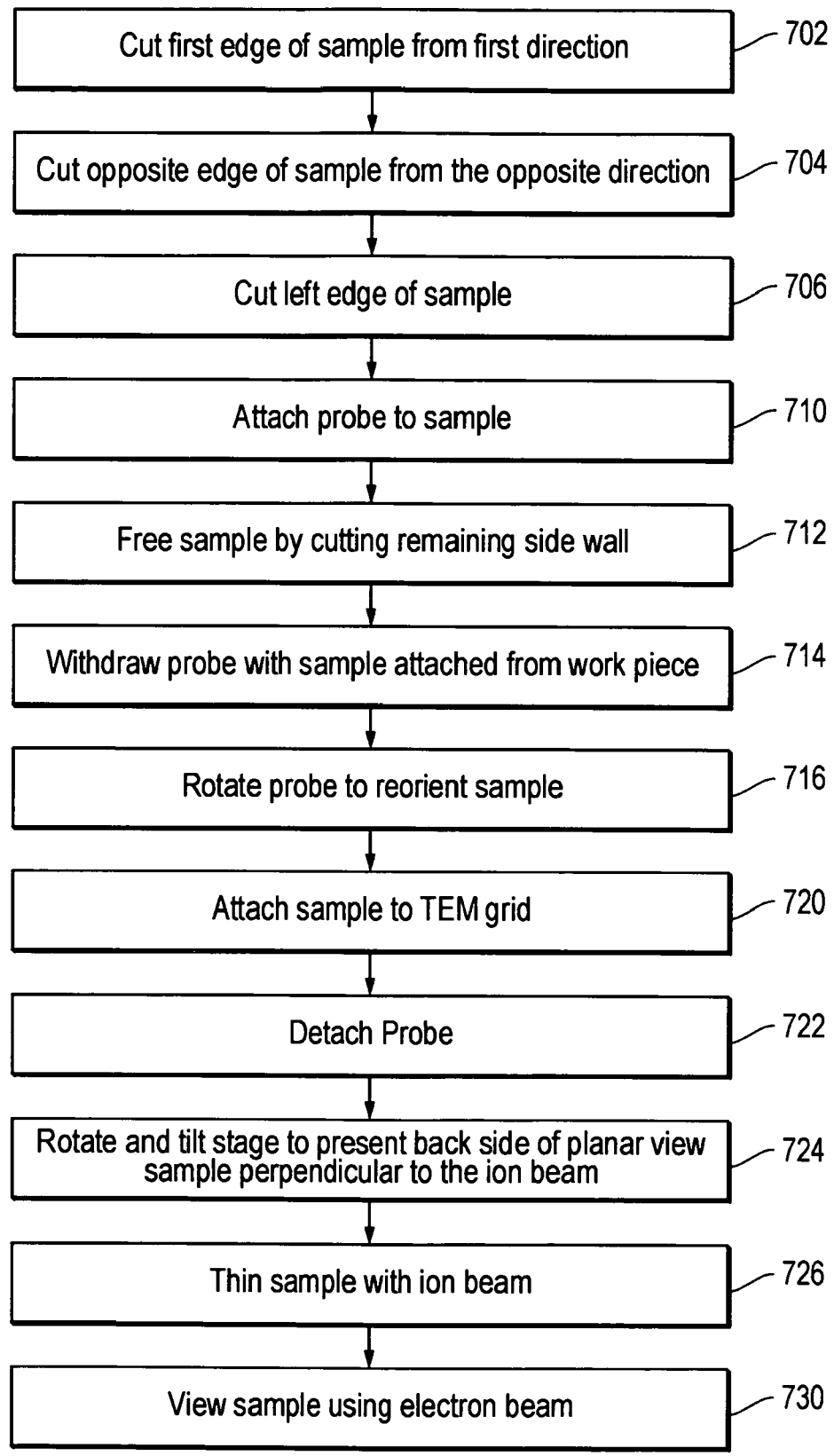
FIG. 7 is a flow chart showing the steps of a preferred embodiment of the present invention.

FIG. 7 describes the steps of a preferred method of preparing a planar view TEM sample. FIG. 5 as described above shows the results of some of the initial steps of FIG. 7. In step 702 a focused ion beam makes a first cut 506A from a first direction in work piece 500 under a sample to be extracted. In step 704, the ion beam makes a second cut 506B under the sample from a second direction, opposite to the first direction and intersecting first cut 506A. For example, the sample stage can be rotated 180 degrees and the angle of incidence for the first and second cuts can be the same. In step 706, a left edge is cut 508A intersecting previous cuts 506A and 506B.

Figure 8:
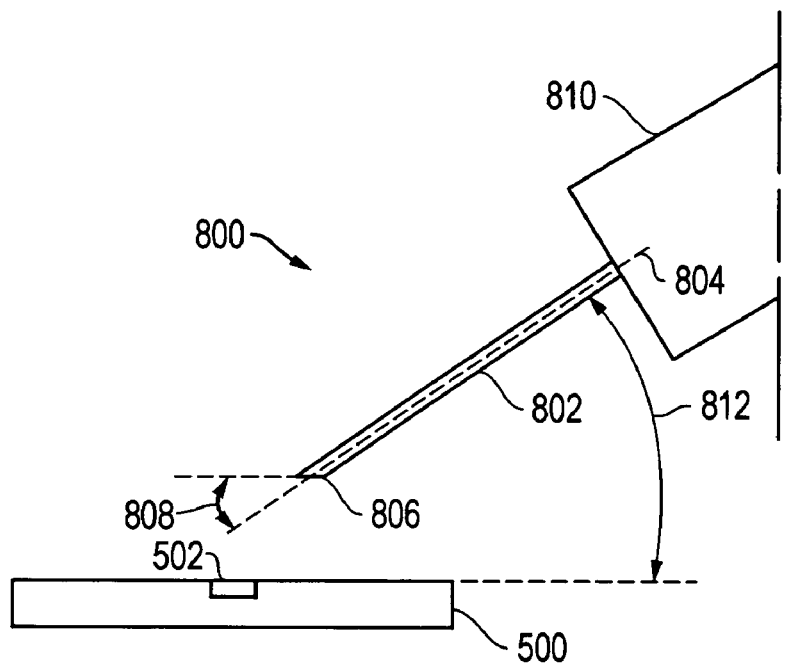
FIG. 8 shows a probe used in a preferred embodiment of the invention.
Figure 9:
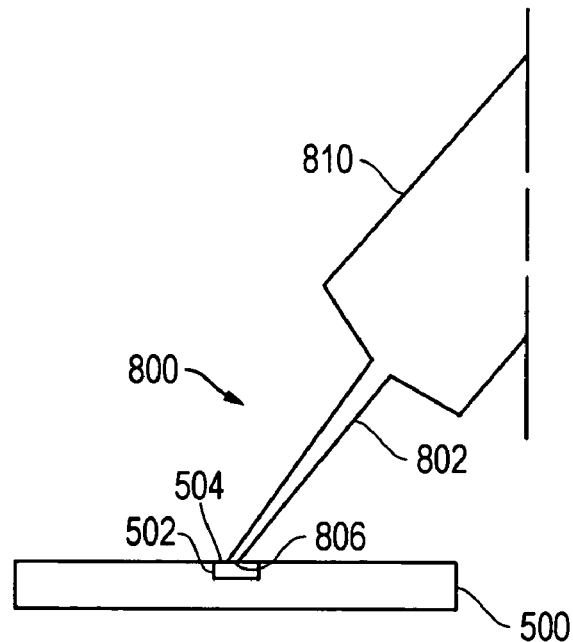
FIG. 9 shows the probe of FIG. 8 positioned at the sample 502.

FIG. 8 shows a probe 800 comprising a shaft 802 having a longitudinal axis 804 and a tip 806 cut at an angle 808 to the longitudinal axis 804. Probe shaft 802 is attached to a micromanipulator 810, which can move the shaft in three dimensions and can rotate the shaft. The shaft preferably remains at a fixed angle 812, preferably 45 degrees, to the plane of the sample stage in its untilted orientation. The probe tip 808 is preferably cut at the same angle as angle 812, so that the flat area of the probe tip is parallel to the plane of the sample stage in its untilted orientation. In step 710, probe tip 806 is attached to the sample 502 as shown in FIG. 9. The probe 800 can be attached, for example, using focused ion beam deposition of a metal, such as tungsten, to the sample and the probe. To attach the probe 800 to the sample 502, the probe tip 806 is brought into contact with the sample 502 on major surface 504. A precursor gas, such as tungsten hexacarbonyl, $W(CO)_6$, is directed toward the point of contact between the probe tip 806 and the sample 502, as the ion beam is directed to scan the area around the point of contact. The ion beam is used to induce decomposition of the precursor gas to deposit a material that connects the sample 502 to the probe tip 806.

Figure 10:
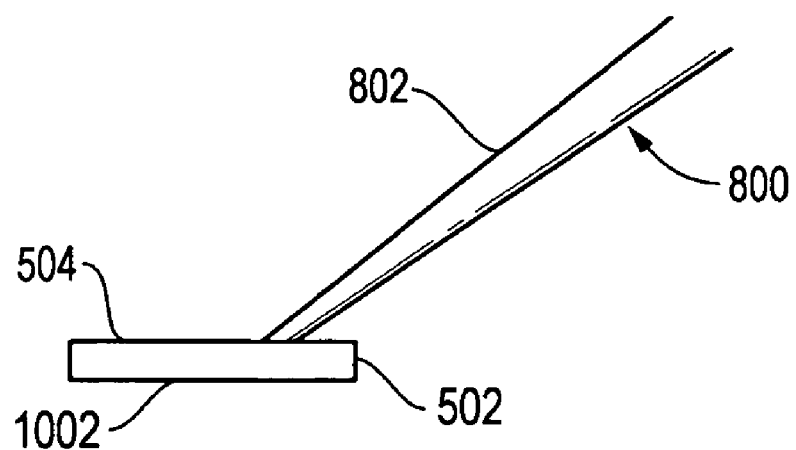
FIG. 10 shows the probe of FIG. 8 with a sample attached.

In step 712, the right side wall 508B of the sample is cut, freeing the sample 502. Alternatively, probe 800 can be attached to the sample 502 after the right side wall 508B is cut and the sample is freed. Next, the probe 800 is withdrawn in step 714 to separate the sample 502 from the work piece 500. FIG. 10 shows the sample 502 attached to the probe 800 on major surface 504, opposite to a wedge-shaped backside 1002.

Figure 11:
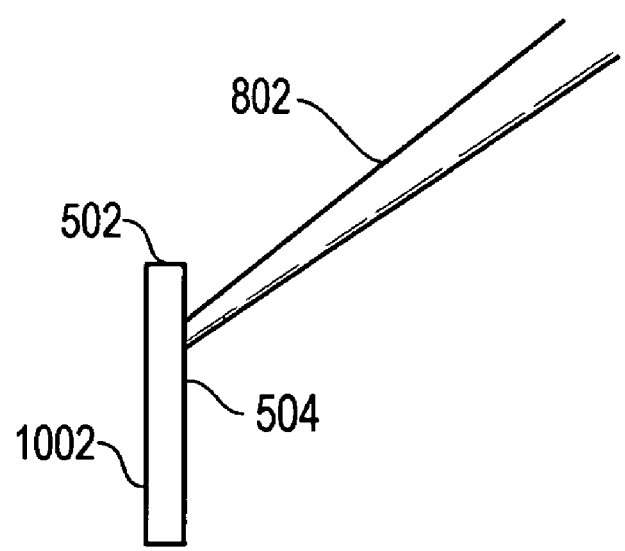
FIG. 11 shows the probe of FIG. 10 rotated 180 degrees to change the orientation of the sample.
Figure 12:
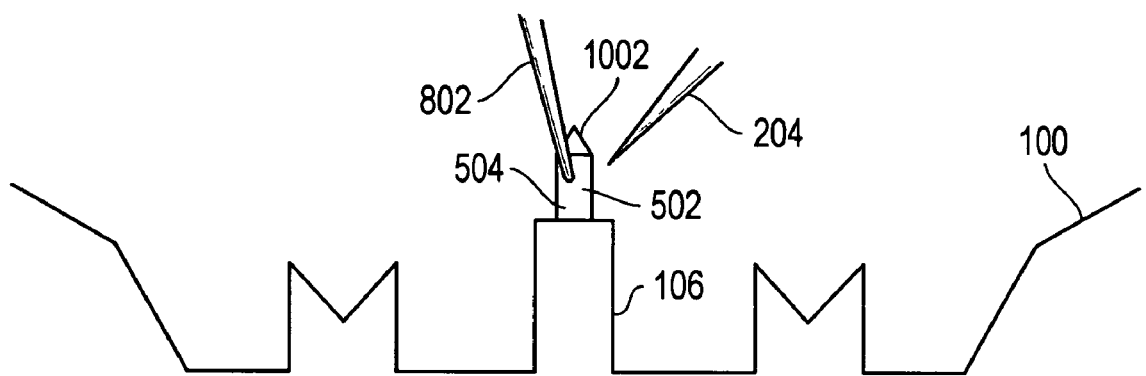
FIG. 12 shows a sample of FIG. 11 being attached to a TEM grid.
Figure 13:
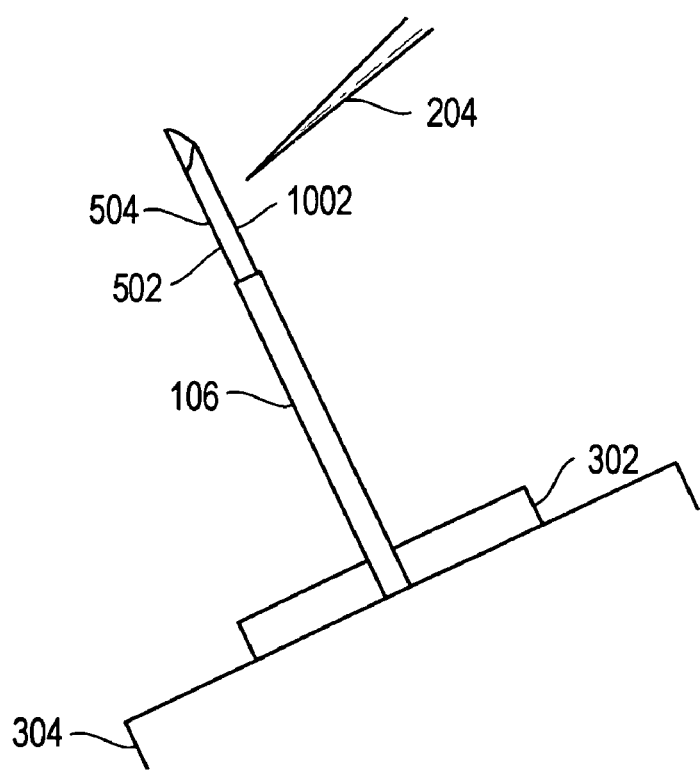
FIG. 13 shows the TEM grid of FIG. 12 on a stage that has been rotated and tilted to orient the sample for ion beam thinning.
Figure 14:
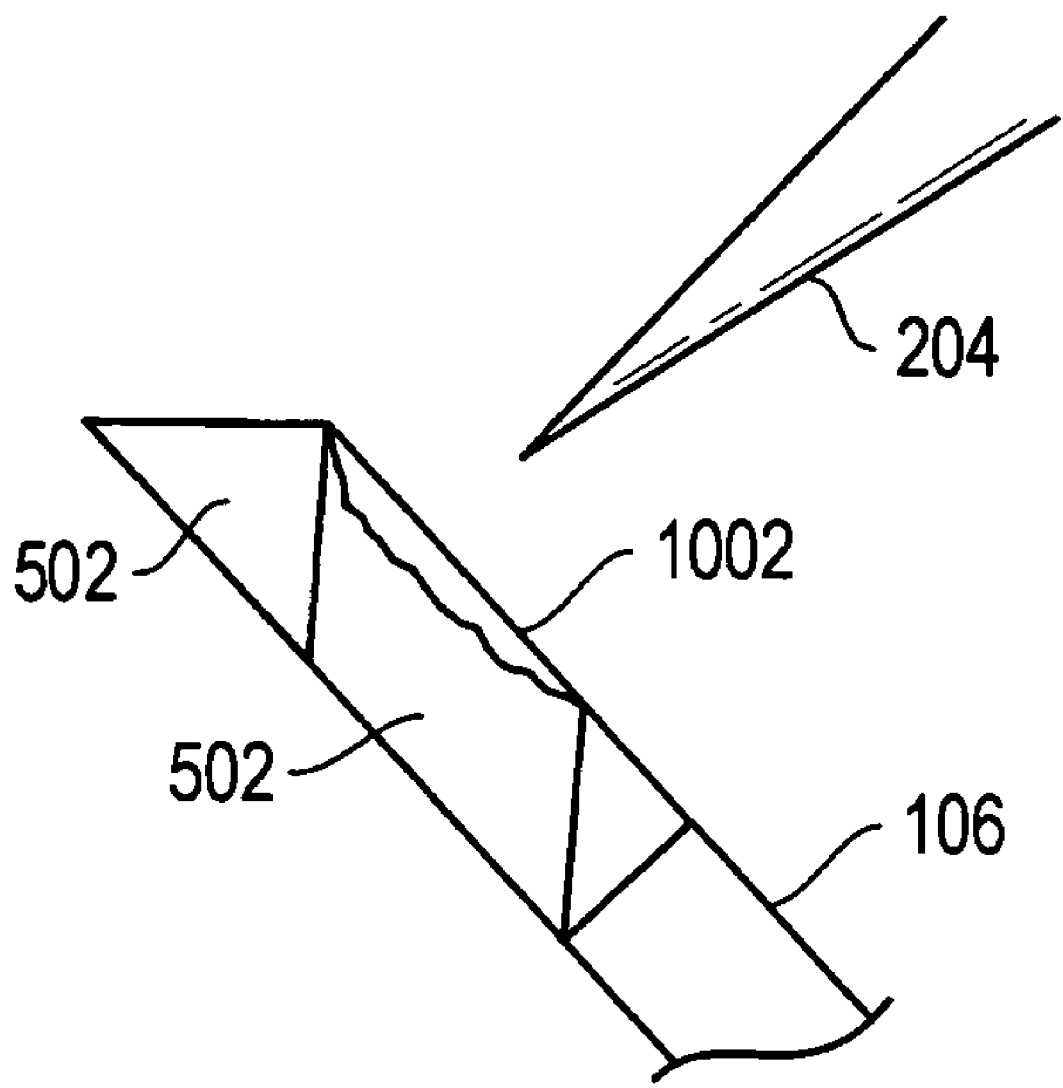
FIG. 14 shows the sample of FIG. 3 partly thinned.

To view sample 502 on a TEM, wedge-shaped backside 1002 must be thinned to reduce the thickness in the center of the wedge. In step 716, the probe shaft 802 is rotated 180 degrees by manipulator 810 as shown in FIG. 11. The major surface 504 is then oriented perpendicular to the plane of sample stage 304 and parallel to the plane of a vertically oriented TEM sample holder. The sample 502 is then attached using ion beam deposition in step 720 to a finger 106 of the vertically oriented TEM grid 100 as shown in FIG. 12. The probe 802 is detached from the sample 502 in step 722, typically using the FIB to sever the connection. In step 724, the sample stage 304 is rotated as shown in FIG. 13 so that the back side 1002 is facing the ion beam 204, and sample stage 304 is tilted so that back side 1002 is perpendicular to the ion beam. The sample is now oriented in a suitable position for thinning by ion beam machining of back side 1002. In step 726, the back side 1002 of sample 502 is thinned as shown in FIG. 14. In step 730, the sample is observed in a TEM or an STEM.

Skilled persons will also recognize that the flat surface on the bottom of the probe, while preferred, can be eliminated in some embodiments. As long as the sample is fixed to the probe, rotating the probe will re-orient the sample, with the re-orientation angle being determined by the degree of rotation and the angle between the probe axis and the stage plane. Thus, a rounded probe tip, a probe tip angle in which the probe tip is not parallel to the stage plane, or any other probe tip shape, is within the scope of the invention.

Although the present invention and its advantages have been described in detail, it should be understood that various changes, substitutions and alterations can be made herein without departing from the spirit and scope of the invention as defined by the appended claims. For example, the angles and orientations described are useful for a system with an ion beam oriented at an angle to the vertical. For an ion beam column that is oriented vertically, or at any other angle, a skilled person can readily alter the example described above to provide an appropriate embodiment of the invention. The invention is useful not only for TEM sample preparation, but can be used for SEM or optical microscope observation, or for any charged particle beam, laser, or other operation on a microscopic specimen.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method for creating a planar view TEM sample, the method comprising:
    providing a substrate on a sample stage having a sample stage plane;
    freeing a sample from the substrate using an ion beam;
    characterized by attaching a probe to the sample, the probe including a shaft having a shaft axis, the shaft axis oriented at a shaft angle in relation to the sample stage plane, the probe having a probe tip including a flat attachment surface, the attachment surface orientated at a non-normal tip angle to the shaft axis, the probe being attached to the sample such that the attachment surface of the probe is parallel to the sample surface;
    rotating the shaft axis through a first rotational angle to rotate the sample attached to the probe tip by an orientational angle;
    attaching the sample to a TEM grid;
    thinning the sample using a charged particle beam; and
    viewing the sample attached to the TEM grid with a TEM or STEM.

2. The method of claim 1 in which the shaft angle is 45 degrees, the tip angle is 45 degrees, the first rotational angle is 180 degrees, and the orientation angle is ninety degrees.

3. The method of claim 1 in which the attachment surface of the tip is oriented parallel to the sample stage plane when the attachment surface of the tip is attached to the sample.

4. The method of claim 3 in which the TEM grid is oriented vertically.

5. The method of claim 1 in which attaching the probe to the sample includes attaching the probe to the sample by ion beam deposition.

6. The method of claim 1 in which attaching the probe to the sample includes attaching the probe to the sample by an adhesive.

7. The method of claim 1 of claim 1 in which freeing a sample from a substrate using a charged particle beam includes freeing a sample from a substrate using a focused ion beam.

8. An apparatus for processing a sample, comprising
    a charged particle beam column;
    a sample stage having a sample stage plane, the sample stage capable of moving in at least two dimensions, rotating about a vertical axis, and tilting away from the horizontal;
    a probe including a probe shaft having a shaft axis and a probe tip at the end of the probe shaft, the probe tip including a flat attachment surface for attachment to a sample, said attachment surface oriented at an attachment surface angle that is at a non-normal angle to the shaft axis;
    a micromanipulator for holding and rotating the probe along the shaft axis, the micromanipulator holding the shaft at a shaft angle relative to the sample stage plane, the micromanipulator having a shaft rotation capability such that when the micromanipulator rotates the probe shaft by a shaft rotation angle, the orientation of the probe attachment surface is changed by a sample orientation change angle.

9. The apparatus of claim 8 in which the charged particle beam column is a focused ion beam column.

10. The apparatus of claim 8 in which the micromanipulator holds the shaft oriented at 45 degrees to the sample stage, the flat surface of the probe tip being oriented parallel to the sample stage plane.

11. A method of manipulating a sample in a beam system, comprising:
    providing a substrate on a sample stage having a sample stage plane;
    freeing a sample from a substrate;
    attaching a probe to the sample, the probe including a shaft having a shaft axis, the shaft axis oriented at a shaft angle in relation to the sample stage plane and the sample having a major surface that is not parallel to the shaft axis; and
    rotating the shaft about its axis through a first angle to rotate the sample attached to the probe by an orientational angle.

12. The method of claim 11 further comprising attaching the sample to a sample holder.

13. The method of claim 12 further comprising thinning the sample using an ion beam while the sample is attached to the sample holder.

14. The method of claim 13 in which the sample holder comprises a TEM sample holder.

15. The method of claim 11 in which the probe includes a probe tip having a flat surface and in which attaching the probe to the sample includes attaching the probe with the flat surface of the probe parallel to the sample surface.

16. The method of claim 12 in which rotating the shaft axis through a first angle includes rotating the shaft axis by 180 degrees to rotate the sample attached to the probe tip by an orientational angle of 90 degrees.

17. The method of claim 11 further comprising viewing the rotated sample using a scanning electron microscope.

* * * * *